United States Patent
Stokes et al.

(10) Patent No.: US 7,615,004 B2
(45) Date of Patent: Nov. 10, 2009

(54) ENDOSCOPIC ANCILLARY ATTACHMENT DEVICES

(75) Inventors: Michael J. Stokes, Cincinnati, OH (US); Mark S. Ortiz, Milford, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 469 days.

(21) Appl. No.: 11/278,016

(22) Filed: Mar. 30, 2006

(65) Prior Publication Data

US 2007/0232850 A1    Oct. 4, 2007

(51) Int. Cl.
*A61B 1/00* (2006.01)
(52) U.S. Cl. .................................. 600/104; 600/101
(58) Field of Classification Search .............. 600/101, 600/102, 104, 106, 114, 121, 123, 125, 153; 604/164.01, 166.01, 533, 534; 248/682, 248/689, 565, 618, 524, 207, 220.41, 200.43, 248/229.1, 229.2; 403/53, 62, 83, 164, 166, 403/198, 196, 261, 348, 349, 373
See application file for complete search history.

(56) References Cited

U.S. PATENT DOCUMENTS

| | | | |
|---|---|---|---|
| 2,004,013 A | 6/1935 | Reed | |
| 2,004,014 A | 6/1935 | Sanford | |
| 2,004,172 A | 6/1935 | Niday | |
| 4,841,888 A | 6/1989 | Mills et al. | |
| 5,041,129 A | 8/1991 | Hayhurst et al. | |
| 5,080,663 A | 1/1992 | Mills et al. | |
| 5,217,486 A | 6/1993 | Rice et al. | |
| 5,259,366 A | 11/1993 | Reydel et al. | |
| 5,269,809 A | 12/1993 | Hayhurst et al. | |
| 5,376,101 A | 12/1994 | Green et al. | |
| 5,398,670 A | 3/1995 | Ortiz et al. | |
| 5,437,681 A | 8/1995 | Meade et al. | |
| 5,462,558 A | 10/1995 | Kolesa et al. | |
| 5,514,159 A | 5/1996 | Matula et al. | |

(Continued)

FOREIGN PATENT DOCUMENTS

EP    1586275    10/2005

(Continued)

*Primary Examiner*—John P Leubecker
*Assistant Examiner*—Samuel Candler
(74) *Attorney, Agent, or Firm*—Nutter McClennen & Fish LLP

(57) ABSTRACT

Methods and devices are provided for attaching one or more ancillary devices to an endoscope. The ancillary device can be any device that is used in conjunction with endoscopic procedures, such as, by way of non-limiting example, an accessory channel, tube, or sleeve, an indwelling tube or feeding tube, and surgical tools such as graspers, snares, etc. The ancillary device(s) can be positioned adjacent to and along side an external surface of an insertion portion of an endoscope for inserting into a body lumen, and one or more attachment devices can be used to mate the ancillary device(s) to the endoscope at one or more attachment locations. In use, the attachment device(s) will allow the ancillary device to move in coordination with the endoscope, thus allowing the endoscope and the ancillary device(s) to be introduced and guided through a tortuous pathway. In certain exemplary embodiments, the attachment device(s) can be configured to prevent radial movement, i.e., twisting, of the ancillary device relative to the endoscope, yet allow axial sliding of the ancillary device relative to the endoscope.

14 Claims, 6 Drawing Sheets

U.S. PATENT DOCUMENTS

| | | | |
|---|---|---|---|
| 5,540,705 | A | 7/1996 | Meade et al. |
| 5,571,119 | A | 11/1996 | Atala |
| 5,584,861 | A | 12/1996 | Swain et al. |
| 5,709,693 | A | 1/1998 | Taylor |
| 5,713,910 | A | 2/1998 | Gordon et al. |
| 5,755,730 | A | 5/1998 | Swain et al. |
| 5,814,071 | A | 9/1998 | McDevitt et al. |
| 5,860,992 | A | 1/1999 | Daniel et al. |
| 5,887,594 | A | 3/1999 | LoCicero, III |
| 5,899,921 | A | 5/1999 | Caspari et al. |
| 5,902,321 | A | 5/1999 | Caspari et al. |
| 6,010,515 | A | 1/2000 | Swain et al. |
| 6,036,694 | A | 3/2000 | Goble et al. |
| 6,071,233 | A | 6/2000 | Ishikawa et al. |
| 6,200,329 | B1 | 3/2001 | Fung et al. |
| 6,309,346 | B1 | 10/2001 | Farhadi |
| 6,346,111 | B1 | 2/2002 | Gordon et al. |
| 6,358,259 | B1 | 3/2002 | Swain et al. |
| 6,443,962 | B1 | 9/2002 | Gaber |
| 6,454,778 | B2 | 9/2002 | Kortenbach |
| 6,494,888 | B1 | 12/2002 | Laufer et al. |
| 6,500,195 | B2 | 12/2002 | Bonutti |
| 6,506,196 | B1 | 1/2003 | Laufer |
| 6,524,328 | B2 | 2/2003 | Levinson |
| 6,540,789 | B1 | 4/2003 | Silverman et al. |
| 6,558,400 | B2 | 5/2003 | Deem et al. |
| 6,572,629 | B2 | 6/2003 | Kalloo et al. |
| 6,663,639 | B1 | 12/2003 | Laufer et al. |
| 6,719,763 | B2 | 4/2004 | Chung et al. |
| 6,746,460 | B2 | 6/2004 | Gannoe et al. |
| 6,755,843 | B2 | 6/2004 | Chung et al. |
| 6,773,440 | B2 | 8/2004 | Gannoe et al. |
| 6,773,441 | B1 | 8/2004 | Laufer et al. |
| 6,821,858 | B2 | 11/2004 | Namatame et al. |
| 6,835,200 | B2 | 12/2004 | Laufer et al. |
| 6,869,395 | B2 | 3/2005 | Page et al. |
| 6,908,427 | B2 | 6/2005 | Fleener et al. |
| 6,955,643 | B2 | 10/2005 | Gellman et al. |
| 6,976,979 | B2 * | 12/2005 | Lawrence et al. ............ 604/524 |
| 7,431,694 | B2 * | 10/2008 | Stefanchik et al. .......... 600/104 |
| 7,497,844 | B2 * | 3/2009 | Spear et al. ............ 604/164.01 |
| 2001/0023352 | A1 | 9/2001 | Gordon et al. |
| 2002/0107530 | A1 | 8/2002 | Sauer et al. |
| 2002/0193809 | A1 | 12/2002 | Meade et al. |
| 2003/0032967 | A1 | 2/2003 | Park et al. |
| 2003/0083674 | A1 | 5/2003 | Gibbens |
| 2003/0109900 | A1 | 6/2003 | Martinek |
| 2003/0120265 | A1 | 6/2003 | Deem et al. |
| 2003/0120292 | A1 | 6/2003 | Park et al. |
| 2003/0130564 | A1 | 7/2003 | Martone et al. |
| 2003/0171650 | A1 * | 9/2003 | Tartaglia et al. ............ 600/114 |
| 2003/0171760 | A1 | 9/2003 | Gambale |
| 2003/0181924 | A1 | 9/2003 | Yamamoto et al. |
| 2003/0195387 | A1 * | 10/2003 | Kortenbach et al. ......... 600/104 |
| 2003/0225312 | A1 | 12/2003 | Suzuki et al. |
| 2003/0229296 | A1 | 12/2003 | Ishikawa et al. |
| 2003/0233104 | A1 | 12/2003 | Gellman et al. |
| 2003/0233108 | A1 | 12/2003 | Gellman et al. |
| 2004/0002720 | A1 | 1/2004 | Kortenbach et al. |
| 2004/0006351 | A1 | 1/2004 | Gannoe et al. |
| 2004/0024386 | A1 | 2/2004 | Deem et al. |
| 2004/0034369 | A1 | 2/2004 | Sauer et al. |
| 2004/0059350 | A1 | 3/2004 | Gordon et al. |
| 2004/0082963 | A1 | 4/2004 | Gannoe et al. |
| 2004/0098050 | A1 | 5/2004 | Foerster et al. |
| 2004/0122452 | A1 | 6/2004 | Deem et al. |
| 2004/0122453 | A1 | 6/2004 | Deem et al. |
| 2004/0122473 | A1 | 6/2004 | Ewers et al. |
| 2004/0147958 | A1 | 7/2004 | Lam et al. |
| 2004/0162568 | A1 | 8/2004 | Saadat et al. |
| 2004/0193184 | A1 | 9/2004 | Laufer et al. |
| 2004/0194790 | A1 | 10/2004 | Laufer et al. |
| 2004/0210243 | A1 | 10/2004 | Gannoe et al. |
| 2004/0215058 | A1 | 10/2004 | Zirps et al. |
| 2004/0230095 | A1 * | 11/2004 | Stefanchik et al. .......... 600/104 |
| 2005/0015101 | A1 | 1/2005 | Gibbens et al. |
| 2005/0033319 | A1 | 2/2005 | Gambale et al. |
| 2005/0055038 | A1 | 3/2005 | Kelleher et al. |
| 2005/0070921 | A1 | 3/2005 | Ortiz et al. |
| 2005/0070926 | A1 | 3/2005 | Ortiz |
| 2005/0070931 | A1 | 3/2005 | Li et al. |
| 2005/0070934 | A1 | 3/2005 | Tanaka et al. |
| 2005/0070935 | A1 | 3/2005 | Ortiz |
| 2005/0075653 | A1 | 4/2005 | Saadat et al. |
| 2005/0075654 | A1 | 4/2005 | Kelleher |
| 2005/0119527 | A1 * | 6/2005 | Banik et al. ................. 600/117 |
| 2005/0143760 | A1 | 6/2005 | Imran |
| 2005/0143762 | A1 | 6/2005 | Paraschac et al. |
| 2005/0149067 | A1 | 7/2005 | Takemoto et al. |
| 2005/0165419 | A1 | 7/2005 | Sauer et al. |
| 2005/0171470 | A1 * | 8/2005 | Kucklick et al. ......... 604/96.01 |
| 2005/0192599 | A1 | 9/2005 | Demarais |
| 2005/0192601 | A1 | 9/2005 | Demarais |
| 2005/0203488 | A1 | 9/2005 | Michlitsch et al. |
| 2005/0272975 | A1 * | 12/2005 | McWeeney et al. ......... 600/113 |
| 2006/0089536 | A1 * | 4/2006 | Perez-Cruet et al. ........ 600/210 |
| 2006/0235458 | A1 * | 10/2006 | Belson ...................... 606/191 |

FOREIGN PATENT DOCUMENTS

| | | |
|---|---|---|
| WO | WO-95/19140 | 7/1995 |
| WO | WO-00/61012 | 10/2000 |
| WO | WO-01/10312 | 2/2001 |
| WO | WO-01/66001 | 9/2001 |
| WO | WO-01/89393 | 11/2001 |
| WO | WO-02/096327 | 12/2002 |
| WO | WO-2004/021894 | 3/2004 |
| WO | WO-2005/034729 | 4/2005 |

* cited by examiner

ENDOSCOPIC ANCILLARY ATTACHMENT DEVICES

FIELD OF THE INVENTION

The present invention relates to methods and devices for attaching one or more ancillary devices to an endoscope.

BACKGROUND OF THE INVENTION

Minimally invasive procedures are desirable because such procedures can reduce pain and provide relatively quick recovery times as compared with conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall.

Still less invasive treatments include those that are performed through insertion of an endoscope translumenally, i.e., through a natural body orifice to a treatment site. Examples of this approach include, but are not limited to, cystoscopy, hysteroscopy, esophagogastroduodenoscopy, and colonoscopy. Many of these procedures employ the use of a flexible endoscope during the procedure. Flexible endoscopes often have a flexible, steerable articulating section near the distal end that can be controlled by the user by utilizing controls at the proximal end.

Some flexible endoscopes are relatively small (1 mm to 3 mm in diameter), and may have no integral accessory channel (also called biopsy channels or working channels). Other flexible endoscopes, including gastroscopes and colonoscopes, have integral working channels having a diameter of about 2.0 mm to 3.5 mm for the purpose of introducing and removing medical devices and other accessory devices to perform diagnosis or therapy within the patient. As a result, the accessory devices used by a physician can be limited in size by the diameter of the accessory channel of the scope used. Additionally, the physician may be limited to a single accessory device when using the standard endoscope having one working channel.

Certain specialized endoscopes are available, such as large working channel endoscopes having a working channel of 5 mm in diameter, which can be used to pass relatively large accessories, or to provide capability to suction large blood clots. Other specialized endoscopes include those having two working channels. One disadvantages of such large diameter/multiple working channel endoscopes can be that such devices can be relatively expensive. Further, such large diameter/multiple working channel endoscopes can have an outer diameter that makes the endoscope relatively stiff, or otherwise difficult to intubate.

It is thus often desirable to position an ancillary device, such as a tool or a working channel for receiving a tool, alongside an external surface an endoscope. While various techniques are known for attaching ancillary devices to an endoscope, one drawback of current techniques is the potential for the ancillary device to move as the endoscope is inserted through a tortuous pathway. This can affect the surgeon's ability to control the device and to maintain the device within a desired field of view of the imaging capability of the endoscope.

Accordingly, there remains a need for improved methods and devices for attaching an one or more ancillary devices to an endoscope.

SUMMARY OF THE INVENTION

The present invention provides methods and devices for attaching an ancillary device, such as an accessory channel or a surgical tool, to an endoscope. In one exemplary embodiment, an ancillary attachment device is provided and includes a clamp having an axial pathway formed therethrough and configured to receive an endoscope and an ancillary device. The axial pathway is expandable to allow the clamp to expand to be positioned radially around an endoscope and an ancillary device extending axially adjacent to the endoscope, and to allow the clamp to close around the endoscope and the ancillary device to mate and maintain the ancillary device in a substantially fixed position relative to the endoscope.

While the clamp can have a variety of configurations, in one embodiment the clamp can include a plurality of segments spaced axially apart from one another and defining the axial pathway extending therethrough. In certain exemplary embodiments, each segment can include a tool engaging portion adapted to be disposed radially around and to engage a shaft of an endoscope, and a tool seating portion adapted to seat an ancillary device therein to attach the ancillary device to the endoscope. The tool engaging portion can be in the form of a ring-shaped member, and the tool seating portion can be in the form of a protrusion formed in the ring-shaped member and defining a groove for seating a portion of an ancillary device. In use, the tool seating portion can maintain an ancillary device in a fixed radial position relative to an endoscope. In another embodiment, each segment can include first and second terminal ends that overlap to form a circular member. At least one of the terminal ends of each segment can be mated to one another. In other embodiments, the clamp can be in the form of a coiled body having a plurality of successive turns, with each turn of the coiled body forming a segment. The clamp can also include a variety of other features to facilitate mating of an ancillary device to an endoscope. For example, the clamp include a coating disposed on at least a portion of an internal surface of the clamp to prevent slippage between the clamp and an endoscope and/or ancillary device extending therethrough.

In another embodiment, an endoscopic kit is provided and includes an endoscope having an elongate shaft with a viewing element located at a distal end thereof, an ancillary device configured to be positioned axially adjacent to the endoscope, and at least one attachment device having a plurality of axially spaced, expandable segments sized to be disposed radially around a portion of the endoscope and the ancillary device to mate the ancillary device to the endoscope. The attachment device can be adapted to maintain the ancillary device in a substantially fixed radial position relative to the endoscope, yet to allow axial sliding of the ancillary device relative to the endoscope. In an exemplary embodiment, the kit includes a plurality of attachment devices for mating an ancillary device to an endoscope at a plurality of locations.

A method for attaching an ancillary device to an endoscope is also provided, and in one embodiment the method can include positioning an ancillary device axially adjacent to an elongate insertion portion of an endoscope, and positioning at least one radially expandable attachment device radially around the endoscope and the ancillary device to attach the ancillary device to the endoscope such that the ancillary device moves in coordination with the endoscope. The attachment device(s) can maintain the ancillary device in a substantially fixed radial position relative to the endoscope, yet allow axial sliding of the ancillary device relative to the endoscope. In an exemplary embodiment, a plurality of radially expandable attachment devices are disposed radially around the endoscope and the ancillary device at a plurality of locations along a length of the endoscope and the ancillary device.

Various techniques can be used to position the attachment device(s) around the endoscope and the ancillary device, and the technique will vary depending on the configuration of the attachment device(s). In one embodiment, the attachment device can have a coiled configuration that is positioned around the endoscope and the ancillary device by rotating the attachment device around the endoscope and the ancillary device. In another embodiment, the attachment device can include a plurality of ring-shaped segments each having first and second terminal ends. The attachment device can be positioned around the endoscope and the ancillary device by separating the terminal ends of each segment to expand the attachment device, and positioning the expanded attachment device around the endoscope and the ancillary device. The terminal ends of each segment can come together to engage the endoscope and the ancillary device. The attachment device(s) can also include other features, such as a groove formed on an internal surface thereof and adapted to seat the ancillary device therein to maintain the ancillary device in a fixed radially position relative to the endoscope.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for attaching one or more ancillary devices to an endoscope. The ancillary device can be any device that is used in conjunction with endoscopic procedures, such as, by way of non-limiting example, an accessory channel, tube, or sleeve, an indwelling tube or feeding tube, and surgical tools such as graspers, snares, etc. The ancillary device(s) can be positioned adjacent to and along side an external surface of an insertion portion of an endoscope for inserting into a body lumen, and one or more attachment devices can be used to mate the ancillary device(s) to the endoscope at one or more attachment locations. In use, the attachment device(s) will allow the ancillary device to move in coordination with the endoscope, thus allowing the endoscope and the ancillary device(s) to be introduced and guided through a tortuous pathway. In certain exemplary embodiments, the attachment device(s) can be configured to prevent radial movement, i.e., twisting, of the ancillary device relative to the endoscope, yet allow axial sliding of the ancillary device relative to the endoscope. A person skilled in the art will appreciate that the term "endoscope" as used herein is intended to include any endoscopic or laparoscopic viewing apparatus.

Figure 1A:
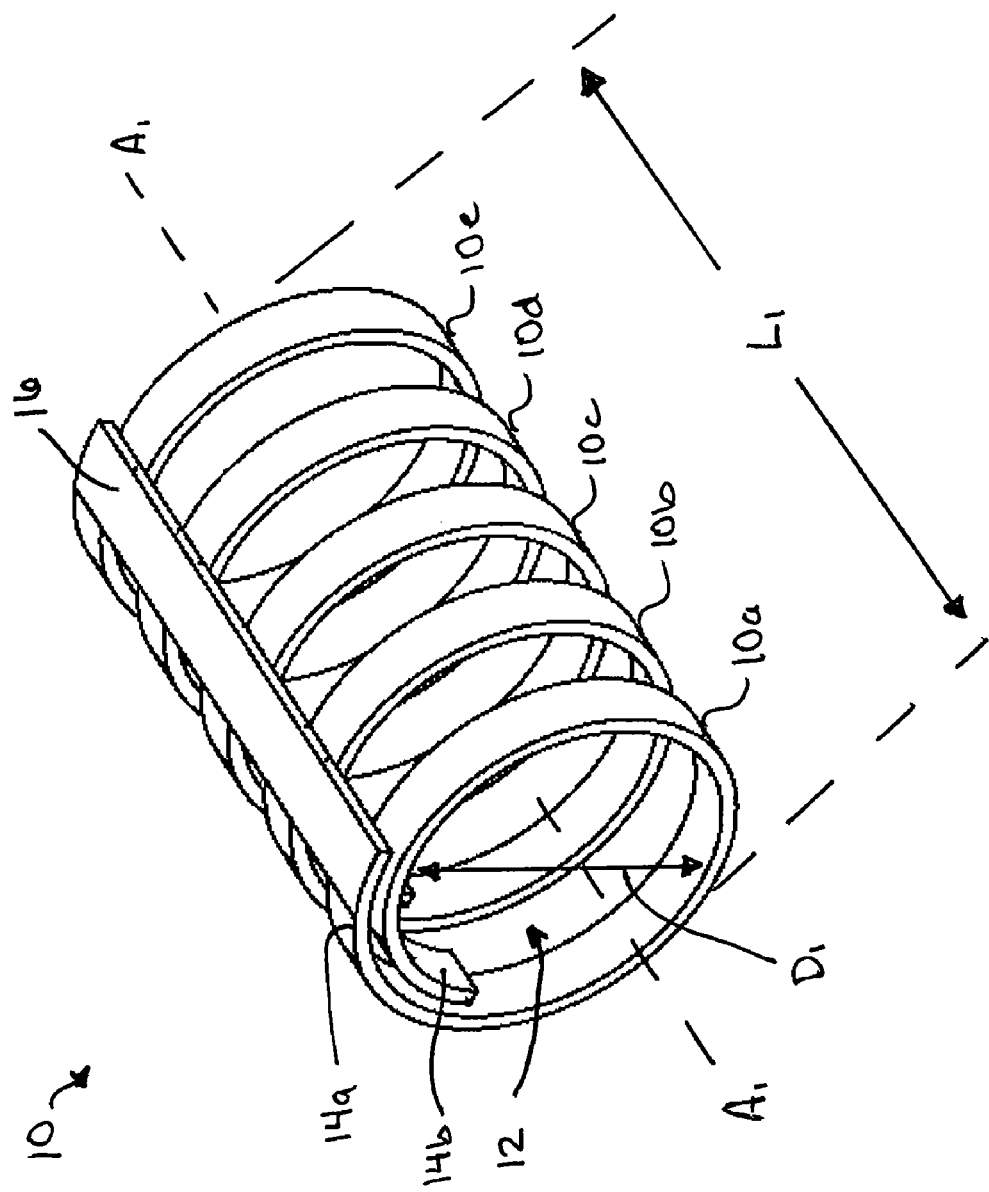
FIG. 1A is a perspective view of one embodiment of an ancillary attachment device for attaching an ancillary device to an endoscope.

FIG. 1A illustrates one exemplary embodiment of an ancillary attachment device 10 for attaching one or more ancillary devices to an endoscope. In general, the attachment device 10 is in the form of an elongate body formed from a plurality of segments 10a, 10b, 10c, 10d, 10e that are spaced apart from one another along an axis $A_1$ of the attachment device 10. The segments 10a-e define a pathway 12 formed therethrough for receiving an endoscope and one or more ancillary devices therein. The shape of the segments 10a-e, and thus the shape of the pathway 12, can vary depending on the configuration of the endoscope and ancillary device(s). In the illustrated embodiment, each segment 10a-e is ring shaped with first and second terminal ends (terminal ends 14a, 14b are shown on segment 10a) that overlap to form the ring. Thus, each segment 10a-e has a substantially circular cross-sectional shape. The inner diameter $D_1$ of the segments, and thus the pathway 12, can vary depending on the size of the endoscope and ancillary device(s), as well as the desired strength of the mating connection. For example, the pathway 12 can have an inner diameter $D_1$ that is less than a maximum outer diameter of the endoscope and the ancillary device, such a friction fit is formed between the attachment device 10 and the endoscope and ancillary device. The friction fit can be configured to prevent any movement between the ancillary device and the endoscope. As will be discussed below, other techniques can be used to facilitate engaging between the attachment device 10 and an endoscope and ancillary device(s), and other types of fits can be used such as a slip fit, which allows the ancillary device to slide relative to the endoscope. A person skilled in the art will appreciate that the segments 10a-e can have other cross-sectional shapes such as square, ovular, rectangular, triangular, etc. The segments 10a-e can also have an open configuration. For example, the terminal ends of each segment 10a-e can be spaced apart to form a C-shaped member. A person skilled in the art will appreciate that the attachment device 10 can include only one segment, such that the device is in the form of a single ring-shaped member.

The particular quantity of segments 10a-e can also vary depending on the desired portions of an ancillary device to be attached to an endoscope, and the desired strength of the mating connection between an ancillary device(s) and an endoscope. For example, the attachment device 10 can include numerous segments such that the device 10 has a length $L_1$ that is substantially the same as the length of an insertion portion of an endoscope, thus allowing the ancillary device 10 to be attached to the endoscope along the entire length thereof. Alternatively, the attachment device 10a-e can include a few segments such that only a portion of an ancillary device is attached to an endoscope. With such a configuration, multiple attachment devices can be used and positioned at various locations along the length of an endoscope and an ancillary device, as will be discussed in more detail below. The size of each segment 10a-e, e.g., the width, length, thickness etc., can also vary to obtain a desired mating connection between an ancillary device(s) and an endoscope.

As noted above, the segments 10a-e can be spaced axially apart from one another, i.e., spaced along the axis $A_1$. Such a configuration allows the attachment device 10 to flex axially in coordination with flexion of the endoscope and ancillary device as the devices are inserted through a tortuous pathway, as will also be discussed in more detail below. While various techniques can be used to mate the segments 10a-e and maintain them in an axial spaced relationship, FIG. 1A illustrates a cross-connector bar 16 extending axially along the attachment device 10 and attached to the first end of each segment 10a-e. The cross-connector bar 16 can also facilitate mating of the attachment device 10 around an endoscope and ancillary device(s), as the cross-connector bar 16 can be engaged and pulled into an open configuration wherein the device 10 can be positioned around the endoscope and ancillary device (s).

Figure 1B:
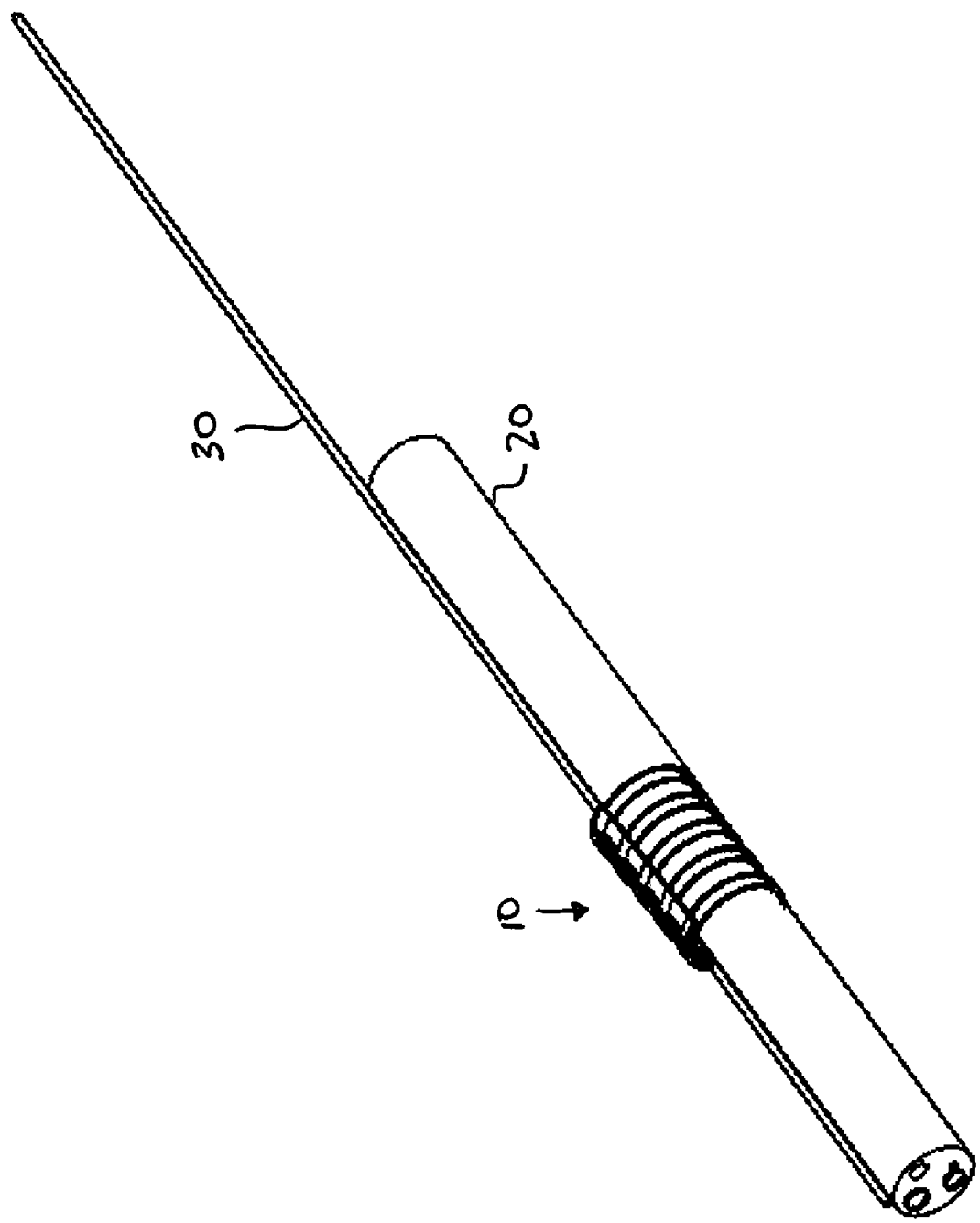
FIG. 1B is a perspective view showing the device of FIG. 1A in use attaching an ancillary device to an endoscope.

FIG. 1B illustrates the attachment device 10 in use disposed around an endoscope 20 and an ancillary device 30 to mate the ancillary device 30 to the endoscope 20. While various techniques can be used to position attachment device 10 radially around the endoscope 20 and the ancillary device 30, in an exemplary embodiment the attachment device 10 is expandable. In particular, the terminal ends of each segment 10a-e can be moved away from one another to form an axial opening in the attachment device 10. This can be achieved by merely grasping and pulling the cross-connector bar 16 away from the device 10 to form an opening between the first and second terminal ends of each segment 10a-e. The attachment device 10 can then be placed radially around the endoscope 20 and the ancillary device 30 and the terminal ends can move together to cause the attachment device 10 to engage the endoscope 20 and ancillary device 30 therein. While each segment 10a-e can include a hinge or other joint formed thereon for allowing the ends to move relative to one another, in an exemplary embodiment the terminal ends are biased to a closed configuration, as shown in FIGS. 1A and 1B. This can be achieved by forming the attachment device 10, or at least the segments 10a-e of the attachment device 10, from a flexible material, such as a plastic or metal. A person skilled in the art will appreciate that a material can be selected to produce an attachment device 10 having a desired amount of strength and flexibility.

Figure 2A:
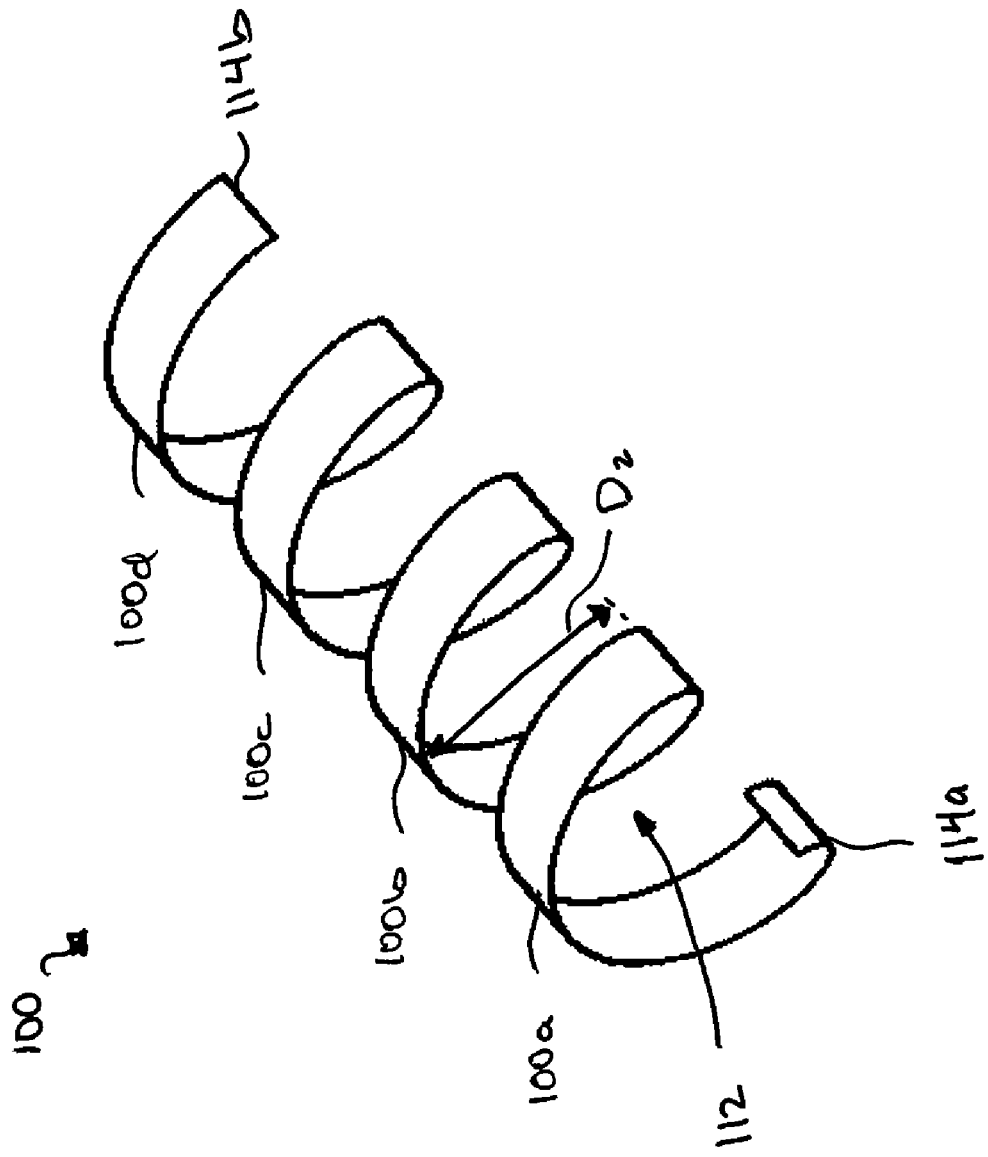
FIG. 2A is a perspective view of another embodiment of an ancillary attachment device for attaching an ancillary device to an endoscope.

FIG. 2A illustrates another embodiment of an attachment device 100 for removably attaching one or more ancillary devices to an endoscope. In this embodiment, the attachment device 100 has a coiled configuration with each successive turn forming a segment 100a-d of the coil. The coiled attachment device 100 also includes first and second terminal ends 114a, 114b formed at opposed ends thereof. As noted above, the number of turns or segments, as well as the amount of spacing between the segments, can be varied to obtain a desired amount of flexibility. In an exemplary embodiment, the device 100 has a flexibility that allows a pathway 112 extending through the device to expand to receive an endoscope and one or more ancillary devices therein, and an inner diameter $D_2$ that allows the device 100 to engage and maintain the ancillary device(s) in close contact with the endoscope, and more preferably in a substantially fixed radial position relative to the endoscope.

Figure 2B:
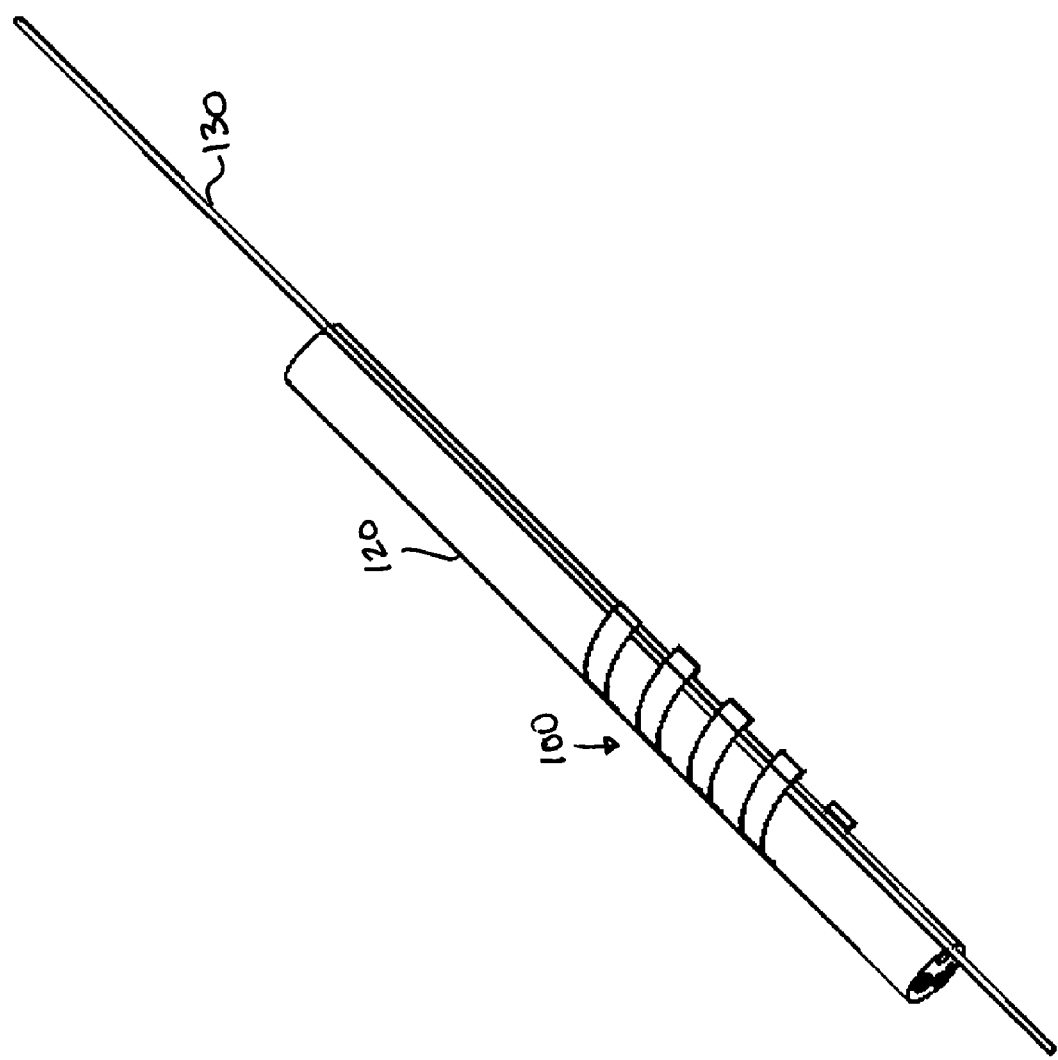
FIG. 2B is a perspective view showing the device of FIG. 2A in use attaching an ancillary device to an endoscope.

FIG. 2B illustrates the device 100 in use disposed around an endoscope 120 and an ancillary device 130. In order to mate the attachment device 100 to the endoscope 120 and the ancillary device 130, the first terminal end 114a of the attachment device 100 can be placed around the endoscope 120 and the ancillary device 130. The attachment device 100 can then be rotated to rotatably place the attachment device 100 around the endoscope 120 and ancillary device 130, thereby mating the ancillary device 130 to the endoscope 120. In an exemplary embodiment, the diameter $D_2$ of the pathway 112 is smaller than a maximum diameter of the endoscope 120 and the ancillary device 130, such that the attachment device 100 is slightly expanded when it is disposed around the endoscope 120 and the ancillary device 130 to form a tight mating connection, such as a friction fit or a slip fit, between the devices. As previously explained with respect to FIGS. 1A and 1B, various materials can be used to form an expandable attachment device.

In other embodiments, the attachment device can include features to help prevent radial movement, i.e., twisting, of the ancillary device about the outer perimeter of the endoscope. By way of non-limiting example, the attachment device can be formed from a non-slip material that is effective to grip the endoscope and the ancillary device. In another embodiment, a portion of the attachment device, such as the inner surface of the device, can include a non-slip surface coating disposed thereon, or can include other surface features, such as gripping teeth or protrusions, that engage the endoscope and the ancillary device. The engagement features or coating can also be disposed or formed on only portions of the attachment device to allow the device to engage the endoscope, yet allow free slidable movement of an ancillary device.

Figure 3A:
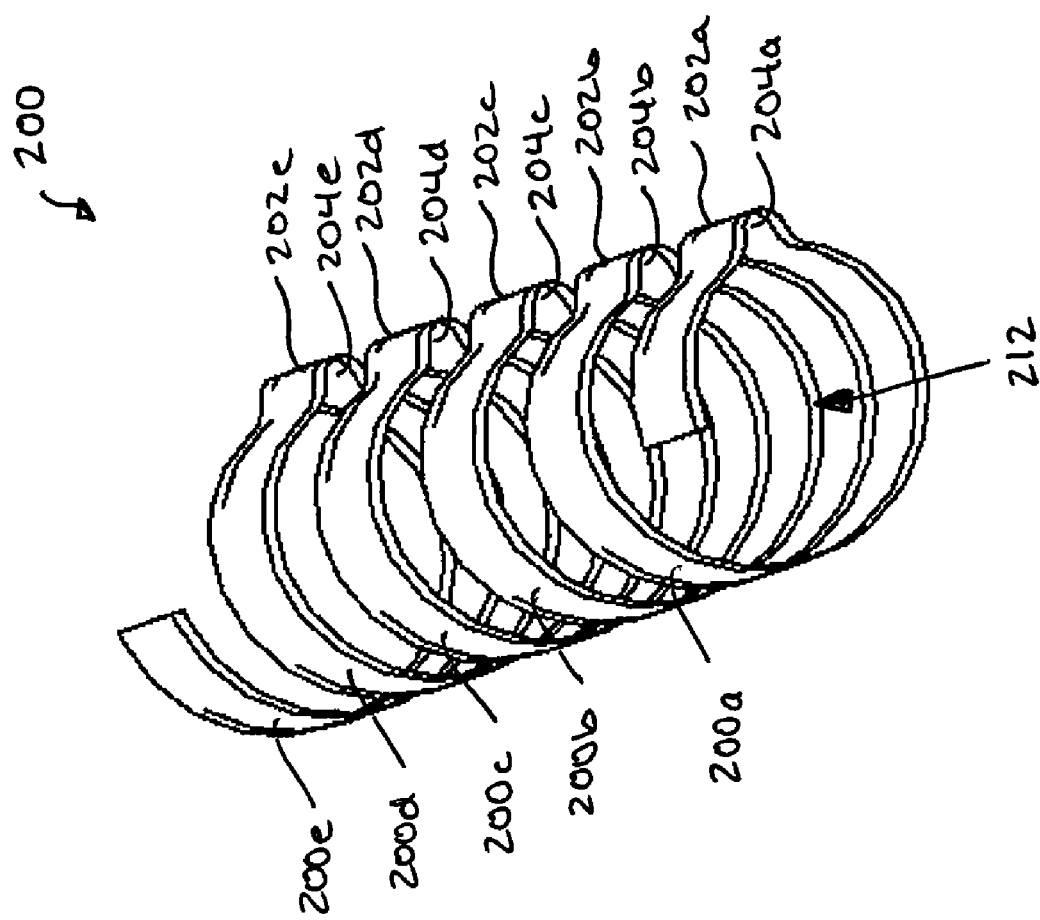
FIG. 3A is a perspective view of yet another embodiment of an ancillary attachment device for attaching an ancillary device to an endoscope.
Figure 3B:
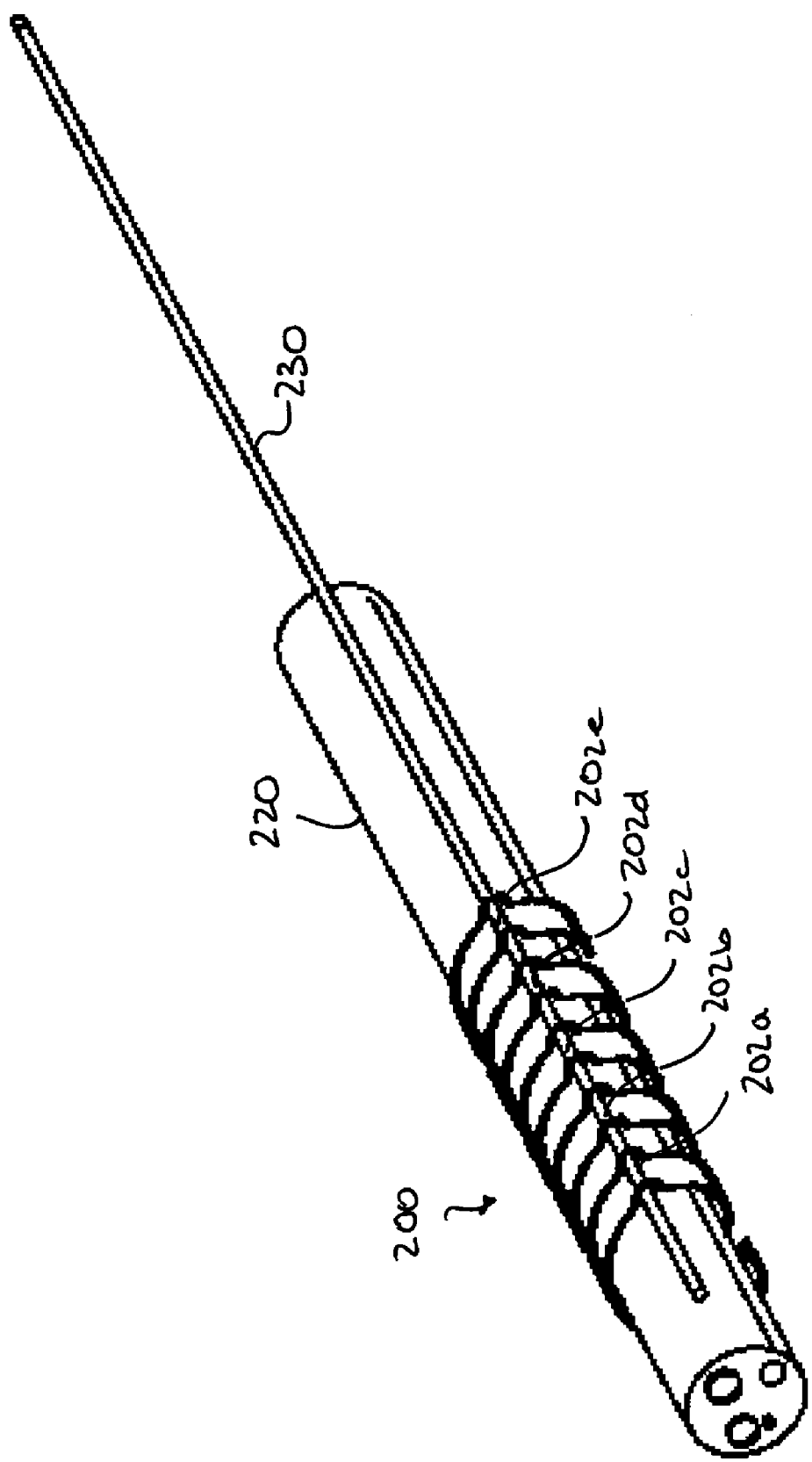
FIG. 3B is a perspective view showing the device of FIG. 3A in use attaching an ancillary device to an endoscope.

FIG. 3A illustrates another embodiment of a technique for preventing radial movement between an endoscope and an ancillary device. As shown, the attachment device 200 is similar to the device 100 of FIG. 2A, and has a coiled configuration with successive turns, each of which forms a segment 200a-e. In this embodiment, however, each segment 200a-e includes a detent 202a-e or protrusion formed therein that defines a groove 204a-e on an inner surface of the segment 200a-e for seating an ancillary device. The grooves 204a-e of the segments 200a-e are aligned axially, such that the ancillary tool can extend axially through the pathway 212 and can sit within each of the grooves 204a-e. In use, as shown in FIG. 3B, the grooves 204a-e will engage the ancillary device 230 and will prevent radial movement of the device 230 relative to the endoscope 220. Thus, the ancillary device 230 will remain in a substantially fixed radial position about the endoscope 220. A person skilled in the art will appreciate that a variety of techniques can be used to substantially prevent movement between the attachment device, the endoscope, and the ancillary device(s).

While FIGS. 1B, 2B, and 3B illustrate a single attachment device disposed around a distal portion of an endoscope and ancillary device, the various attachment devices disclosed herein can be disposed around any portion of an endoscope and one or more ancillary devices to mate the ancillary device (s) to the endoscope at desired mating locations. For example, a kit containing multiple attachment devices can be provided and they can be positioned a distance apart from one another at various locations along a length of an endoscope and an ancillary device, thereby forming various attachment points. Depending on the configuration of each attachment device, the attachment device(s) can prevent radial movement, i.e., twisting, of the ancillary device(s) while allowing axial, i.e., sliding, movement of the ancillary device(s) relative to the endoscope. As a result, the attachment device(s) can allow the ancillary device(s) to move in coordination with the endoscope as it is guided through a tortuous pathway.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An ancillary attachment device, comprising:
a clamp comprising a coiled body having a plurality of continuous successive turns and having an axial pathway formed therethrough configured to receive an endoscope and an ancillary device, the axial pathway being expandable to allow the clamp to expand to be positioned radially around an endoscope and an ancillary device extending axially adjacent to the endoscope, and to allow the clamp to close around the endoscope and the ancillary device to mate and maintain the ancillary device in a substantially fixed position relative to the endoscope, the clamp including a plurality of segments spaced axially apart from one another and defining the axial pathway extending therethrough, each turn of the coiled body comprising a segment, each segment including a tool engaging portion adapted to be disposed radially around and to engage a shaft of an endoscope, and a tool seating portion adapted to seat an ancillary device therein to attach the ancillary device to the endoscope.

2. The device of claim 1, wherein the clamp has a substantially circular cross-sectional shape.

3. The device of claim 1, wherein the tool engaging portion comprises a ring-shaped member, and the tool seating portion comprises a protrusion formed in the ring-shaped member and defining a groove for seating a portion of an ancillary device.

4. The device of claim 1, wherein the tool seating portion is adapted to maintain an ancillary device in a fixed radial position relative to an endoscope.

5. The device of claim 1, further comprising a coating disposed on at least a portion of an internal surface of the clamp to prevent slippage between the clamp and an endoscope and/or ancillary device extending therethrough.

6. An endoscopic kit, comprising:
an endoscope having an elongate shaft with a viewing element located at a distal end thereof;
an ancillary device configured to be positioned axially adjacent to the endoscope; and
at least one attachment device comprising a coiled body having a plurality of continuous successive turns and having a plurality of axially spaced, expandable segments in the form of the turns of the coiled body, that are sized to be disposed radially around a portion of the endoscope and the ancillary device to mate the ancillary device to the endoscope.

7. The kit of claim 6, wherein the at least one attachment device is adapted to maintain the ancillary device in a substantially fixed radial position relative to the endoscope, yet to allow axial sliding of the ancillary device relative to the endoscope.

8. The kit of claim 6, wherein the kit includes a plurality of attachment devices for mating an ancillary device to an endoscope at a plurality of locations.

9. The kit of claim 6, wherein each segment includes a tool engaging portion adapted to be disposed around and to engage a shaft of the endoscope, and a tool seating portion adapted to seat the ancillary device therein to attach the ancillary device to the endoscope.

10. The kit of claim 9, wherein the tool engaging portion comprises a ring-shaped member, and the tool seating portion comprises a protrusion formed in the ring-shaped member and defining a groove for seating a portion of the ancillary device.

11. A method for attaching an ancillary device to an endoscope, comprising:
positioning an ancillary device axially adjacent to an elongate insertion portion of an endoscope; and
positioning at least one radially expandable attachment device having a continuous coiled configuration radially around the endoscope and the ancillary device to attach the ancillary device to the endoscope such that the ancillary device moves in coordination with the endoscope by rotating the attachment device around the endoscope and the ancillary device.

12. The method of claim 11, wherein the at least one attachment device maintains the ancillary device in a substantially fixed radial position relative to the endoscope, yet allows axial sliding of the ancillary device relative to the endoscope.

13. The method of claim 11, wherein a plurality of radially expandable attachment devices are disposed radially around the endoscope and the ancillary device at a plurality of locations along a length of the endoscope and the ancillary device.

14. The method of claim 11, wherein the attachment device includes a groove formed on an internal surface thereof and adapted to seat the ancillary device therein to maintain the ancillary device in a fixed radially position relative to the endoscope.

* * * * *

UNITED STATES PATENT AND TRADEMARK OFFICE
CERTIFICATE OF CORRECTION

| | | |
|---|---|---|
| PATENT NO. | : 7,615,004 B2 | Page 1 of 1 |
| APPLICATION NO. | : 11/278016 | |
| DATED | : November 10, 2009 | |
| INVENTOR(S) | : Stokes et al. | |

It is certified that error appears in the above-identified patent and that said Letters Patent is hereby corrected as shown below:

On the title page,

Item [*] Notice: Subject to any disclaimer, the term of this patent is extended or adjusted under 35 USC 154(b) by 469 days Delete the phrase "by 469 days" and insert -- by 514 days --

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,615,004 B2  Page 1 of 1
APPLICATION NO. : 11/278016
DATED : November 10, 2009
INVENTOR(S) : Stokes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 559 days.

Signed and Sealed this

Nineteenth Day of October, 2010

David J. Kappos
*Director of the United States Patent and Trademark Office*